(12) United States Patent
Igondjo-Tchen Changotade et al.

(10) Patent No.: US 7,951,391 B2
(45) Date of Patent: May 31, 2011

(54) BONE SUBSTITUTE COMPRISING FUCANS AND METHODS OF MAKING AND USE THEREOF

(75) Inventors: Sylvie Igondjo-Tchen Changotade, Chelles (FR); Karim Senni, Aulnay Sous Bois (FR); Alexandrine Foucault-Bertaud, Marseilles (FR); Grégory Korb, Vincennes (FR); Maya Brigitte Baroukh, Paris (FR); Jean-Louis Saffar, Montrouge (FR); Gaston-Jacques Godeau, Antony (FR); Corinne Sinquin, Nantes (FR); Sylvia Colliec-Jouault, Nantes (FR); Patrick Durand, Reze (FR)

(73) Assignees: Universite Rene Descartes Paris 5, Paris (FR); Institut Francais de Recherche pour l'Exploitation de la Mer (IFREMER), Issy-les-Moulineaux (FR)

( * ) Notice: Subject to any disclaimer, the term of this patent is extended or adjusted under 35 U.S.C. 154(b) by 283 days.

(21) Appl. No.: 12/280,352

(22) PCT Filed: Feb. 21, 2007

(86) PCT No.: PCT/FR2007/000310
§ 371 (c)(1),
(2), (4) Date: Aug. 22, 2008

(87) PCT Pub. No.: WO2007/096519
PCT Pub. Date: Aug. 30, 2007

(65) Prior Publication Data
US 2009/0043399 A1    Feb. 12, 2009

(30) Foreign Application Priority Data
Feb. 23, 2006 (FR) .................................. 06 01618

(51) Int. Cl.
*A61F 2/00* (2006.01)
*A61K 36/02* (2006.01)
*A61M 31/00* (2006.01)
*A01N 43/04* (2006.01)

(52) U.S. Cl. ................... 424/423; 424/195.17; 604/522; 514/54

(58) Field of Classification Search ........................ None
See application file for complete search history.

(56) References Cited

U.S. PATENT DOCUMENTS
6,828,307 B1 * 12/2004 Colliec-Jouault et al. ...... 514/54

FOREIGN PATENT DOCUMENTS
| EP | 0 403 377 | 6/1990 |
| EP | 0 846 129 | 8/1996 |
| EP | 1207891 | 9/2000 |
| WO | WO 97/08206 | 3/1997 |
| WO | WO 99/32099 | 7/1999 |
| WO | WO 01/66164 * | 9/2001 |
| WO | WO 02/02051 | 1/2002 |
| WO | WO 03/018033 | 3/2003 |

OTHER PUBLICATIONS

Black et al., "Manufacture of Algal Chemicals",. J. Sci. Food Agric., Mar. 3, 1952, pp. 122-129.
Heymann, D., "Etude in vitro de l'association de cellules osteogenes avec une ceramique en phosphate de calcium macroporeuse", Revue de chirurgie orthopedique, 2001, 87, pp. 8-17.
French Search Report dated Jan. 11, 2007 corresponding to FR 0601618.
International Search Report dated Aug. 30, 2007 corresponding to PCT/FR2007/000310.
Takashi Nishino et al., "Isolation, Purification, and Characterization of Fucose-Containing Sulfated Polysaccharides from the Brown Seaweed", Carbohyd. Res., 186, 119-129, 1989.
Yutaka Kariya et al., "Isolation and partial characterization of fucan sulfates from the body wall of sea cucumber *Stichopus japonicus* and their ability to inhibit osteoclastogenesis", Carbohyd. Res., 339, 1139-1346, 2004.
Olivier Berteau, "Sulfated fucans, fresh perspectives: structures, functions, and biological properties of sulfated fucans and an overview of enzymes active toward this class of polysaccharide", Glycobiology, vol. 13, No. 6, 29R-40R, (2003).

* cited by examiner

*Primary Examiner* — Sandra Saucier
(74) *Attorney, Agent, or Firm* — Young & Thompson

(57) ABSTRACT

The present invention relates to the use of fucans with a weight-average molar mass of between 5000 and 100 000 g/mol, for the purposes of bone grafting, engineering and regeneration.

14 Claims, 10 Drawing Sheets

BONE SUBSTITUTE COMPRISING FUCANS AND METHODS OF MAKING AND USE THEREOF

The present invention relates to the use of fucans with a weight-average molar mass between 5000 and 100 000 g/mol, for the purposes of bone grafting, engineering and regeneration.

Fucans are a family of sulfated polysaccharides (cf. Berteau and Mulloy, Glycobiology, vol. 13, no. 6, pp. 29R-40R, 2003). Fucans are polysaccharides constituted predominantly of sulfate-rich chains of fucose units (homofucan) and of less sulfated chains composed of units of fucose, galactose, xylose and glucuronic acid (xylofucoglucuronans). Fucans can be extracted from algae, in particular from brown algae (Pheophycea) or from marine invertebrates. Once extracted, fucans generally have a weight-average molar mass of greater than 500 000 g/mol. Numerous techniques exist for depolymerizing fucans in order to obtain fucans having a weight-average molar mass of between 5000 and 100 000 g/mol (cf. EP0403377). Numerous therapeutic applications for fucans have been described: anticoagulant (cf. EP0403377), treatment of periodontal pathologies and dermal lesions (cf. WO 99/32099), antithrombotic (cf. WO 01/1565), treatment of arthritis and of osteoarthritis (cf. WO 03/018033).

The filling of bone-substance losses is a problem frequently encountered in osteoarticular pathologies and traumas (bone tumors, after-effects of trauma, degenerative pathologies). The specifications of an ideal bone replacement material include, in particular: 1) good tolerance without infectious risks to the recipient; 2) integration into bone structures in situ; 3) an ability to allow bone neoformation of good quality, having mechanical properties sufficient to support the stresses at the site of implantation. Among these materials, natural or synthetic biomaterials constitute the alternative to bone grafts. The desired properties for these materials are osteoconduction, i.e. the ability to guide bone reconstruction on contact with said materials, and/or osteoinduction, i.e. the ability to stimulate bone formation even at an extraosseous site. Several research approaches (cf. Heymann et al., Review of orthopedic surgery, 2001; 87, 8-17) tend toward improving the osteogenic properties of biomaterials. Combining the biomaterials with extracellular matrix proteins or growth factors having an osteogenic potential is one of the lines of research. These growth factors can be incorporated into the biomaterials and released in vivo, thus potentiating the osteogenesis within said biomaterials. Calcium phosphate (Cap) ceramics have also been considered as systems for delivering pharmacological substances (anticancer agents, antibiotics, etc.). The combining of osteocompetent cells, i.e. cells capable of constituting bone tissue, with bone substitutes is the other main line of research. This "hybrid" combination requires, firstly, a filling substitute and, secondly, an autologous source of osteocompetent cells. These cells can originate from bone explants from which osteoblast cells are isolated. However, this method only makes it possible to obtain a small amount of osteocompetent cells. The osteocompetent cells can also originate from medullary osteoprogenitors capable of differentiating in vitro and in vivo. In this respect, all the bone marrow cells or only the stromal cells may be used. It is also possible to obtain a differentiated osteoblastic clone from the progenitor cells of the marrow. Bone marrow cells injected into a bone site can by themselves fill a calibrated bone defect in rats. The association of bone marrow cells with a CaP ceramic enables the ceramic to acquire an osteoconductive nature. In fact, numerous studies carried out in animals demonstrate ossification within ceramics incubated with autologous bone marrow cells and then implanted at an extraosseous site. Furthermore, the bone marrow cells potentiate the integration of the biomaterial at the bone site. They promote the rapidity and the quality of bone regrowth.

WO 02/02051 describes the use of a polysaccharide excreted by the species *Vibrio diabolicus* in bone healing. The polysaccharide can be used for the preparation of a bone endoprosthesis coating or of an osteoconductive filling material. According to the teaching of WO 02/02051, fucans with a high molecular weight (of the order of 1 million g/mol) have no effect on bone healing.

In view of the insufficiencies and drawbacks of the prior art in terms of bone reconstruction, the inventors gave themselves the aim of providing a bone substitute with improved osteoconductive properties.

Surprisingly, the inventors discovered that this aim could be achieved using a particular family of polysaccharides, namely fucans with a weight-average molar mass of between 5000 and 100 000 g/mol. These fucans are capable of promoting and accelerating the migration and proliferation of osteoblastic cells, and also the synthesis of a new bone extracellular matrix and the mineralization thereof.

A subject of the invention is a bone substitute comprising a biomaterial and fucans with a weight-average molar mass of between 5000 and 100 000 g/mol, in particular between 10 000 and 40 000 g/mol.

The fucans used in the present invention have a weight-average molar mass of between M1 and M2, the weight-average molar masses M1 and M2 being chosen independently of one another, M1 being chosen from the values 5000, 10 000, 15 000, 20 000 and 25 000 g/mol, and M2 being chosen from the values 40 000, 60 000, 80 000, 90 000 and 100 000 g/mol.

Preferably, the fucans are obtained from a brown alga. Those skilled in the art may use the usual techniques for obtaining the fucans used in the present invention. By way of example of techniques that can be used, mention may be made of: techniques by controlled lysis of high-molecular-weight fucans followed by purification by gel chromatography as previously described (cf. EP0403377), or by radical depolymerization of high-molecular-weight fucans as previously described (EP0846129 or WO 97/08206); those skilled in the art will readily adapt the operating conditions in order to obtain the desired weight-average molar mass.

The term "biomaterial" is intended to mean any material dedicated to the replacement of a function or of an organ. It is any nonliving material used in a medical device and aimed at replacing or treating a tissue, an organ or a function.

Typically, to prepare a bone substitute according to the invention, those skilled in the art may use any biomaterial commonly used in bone engineering. By way of example, the biomaterial may comprise one or more materials chosen from the group consisting of titanium, collagen, deproteinized and/or demineralized bone, coral, calcium phosphate ceramic, hydroxyapatite, beta-tricalcium phosphate and bioactive glasses.

Advantageously, a bone substitute according to the invention may also comprise one or more growth factors chosen from the groups comprising fibroblast growth factors (FGFs), transforming growth factors (TGFs), insulin growth factors I (IGFs), platelet derived growth factors (PDGFs), bone morphogenetic proteins (BMPs) and vascular endothelial growth factors (VEGFs).

Preferably, a bone substitute according to the invention may also comprise one or more growth factors chosen from the group consisting of BMPs, FGFs, TGF-beta and VEGFs.

Advantageously, a bone substitute according to the invention may also comprise one or more cytokines chosen from the group consisting of interleukin 1, interleukin 6, interleukin 4, tumor necrosis factor-alpha, granulocyte-macrophage colony-stimulating factor and macrophage colony-stimulating factor.

Typically, the surface of the biomaterial of a bone substitute according to the invention has a coating comprising the fucans.

Those skilled in the art may use the usual techniques for covering the surface of the biomaterial with a coating comprising the fucans. By way of example, those skilled in the art may graft the fucans onto the surface of the biomaterial.

The biomaterial of a bone substitute according to the invention may also be impregnated with the fucans.

Advantageously, a bone substitute according to the invention may also comprise cells chosen from the group consisting of osteocompetent cells derived from the bone marrow, from bone explants or from periosteal explants.

To prepare such bone substitutes, those skilled in the art may perform the colonization of a bone substitute with the desired cells.

According to one embodiment, the invention relates to a culture medium for a cell type chosen from the group consisting of osteocompetent cells derived from the bone marrow, from bone or from the periosteum, comprising fucans with a weight-average molar mass of between 5000 and 100 000 g/mol, in particular between 10 000 and 40 000 g/mol.

Typically, a culture medium according to the invention may also comprise one or more growth factors chosen from the group consisting of fibroblast growth factors (FGFs), transforming growth factors (TGFs), insulin growth factors I (IGFs), platelet derived growth factors (PGFs), bone morphogenetic proteins (BMPs) and vascular endothelial growth factors (VEGFs).

According to one embodiment, the invention relates to the use of the fucans with a weight-average molar mass of between 5000 and 100 000 g/mol, in particular between 10 000 and 40 000 g/mol, for culturing osteocompetent cells derived from the bone marrow, from bone or from the periosteum.

According to one embodiment, the invention relates to a method for culturing cells chosen from the group of osteocompetent cells derived from the bone marrow, from the bone or from the periosteum, characterized in that said cells are cultured in a culture medium described above.

According to one embodiment, the invention relates to a method for culturing osteocompetent cells derived from bone marrow, from bone of from the periosteum, characterized in that said cells are cultured on a bone substitute described above.

According to one embodiment, the invention relates to the use of the fucans with a weight-average molar mass of between 5000 and 100 000 g/mol, in particular between 10 000 and 40 000 g/mol, for the manufacture of a medical device having an activity on bone regeneration.

Typically, such a medical device may be used in orthopedic, parodontal and plastic surgery in order to facilitate bone regeneration and to fill the tissue defects occurring, for example, after a lesion due to a pathology, to an accident or to a surgical procedure.

Such a medical device may, for example, be used as a bone repair or filling material, as a bone graft, as a bone endoprosthesis, or as a dental or osteoarticular implant.

Such a medical device may be used for the treatment of bone pathologies such as, for example, osteoporosis.

Such a medical device may, for example, comprise the fucans, preferably in a hydrated form, for example in the form of a hydrogel, alone or in combination with one or more growth factors chosen from the group consisting of fibroblast growth factors (FGFs), transforming growth factors (TGFs), insulin growth factors I (IGFs), platelet derived growth factors (PDGFs), bone morphogenetic proteins (BMPs) and vascular endothelial growth factors (VEGFs).

Combining the fucans with a growth factor makes it possible to increase the rate of bone regeneration.

Preferably, a medical device according to the invention will comprise fucans in a hydrated form and one or more growth factors chosen from the group of BMPs, FGFs, TGF-beta and VEGFs.

Typically, a medical device according to the invention may comprise a bone substitute according to the invention The content of all the documents cited should be considered to be part of the present description.

The present invention will be illustrated more clearly hereinafter with the aid of the examples which follow. These examples are given only by way of illustration of the subject of the invention, of which they in no way constitute a limitation.

FIG. 1 shows the change in the number of osteoblasts as a function of time in the presence and absence of the fucans.

FIGS. 2a, 2b, 2c, 2d represent photographs of a control culture of osteoblastic cells on which alkaline phosphatase activity is detected. FIGS. 2a, 2b, 2c and 2d represent photographs taken after 8, 15, 30 and 45 days of culture, respectively.

FIGS. 3a, 3b, 3c represent photographs of a culture of osteoblastic cells carried out in the presence of 10 μg/ml of fucans. Alkaline phosphatase activity was detected in the end on the cells in culture. FIGS. 3a, 3b and 3c represent photographs taken after 8, 15 and 30 days of culture, respectively.

FIGS. 4a, 4b, 4c, 4d represent photographs of a control culture of osteoblastic cells (FIGS. 4a and 4c) and of a culture of osteoblastic cells carried out in the presence of 10 μg/ml of fucans (FIGS. 4b and 4d). The mineral deposits are visualized by the Von Kossa reaction carried out in the end after fixing of the cells in culture. FIGS. 4a and 4b represent photographs taken after 30 days of culture. FIGS. 4c and 4d represent photographs taken after 45 days of culture.

EXAMPLES

Figure 1:
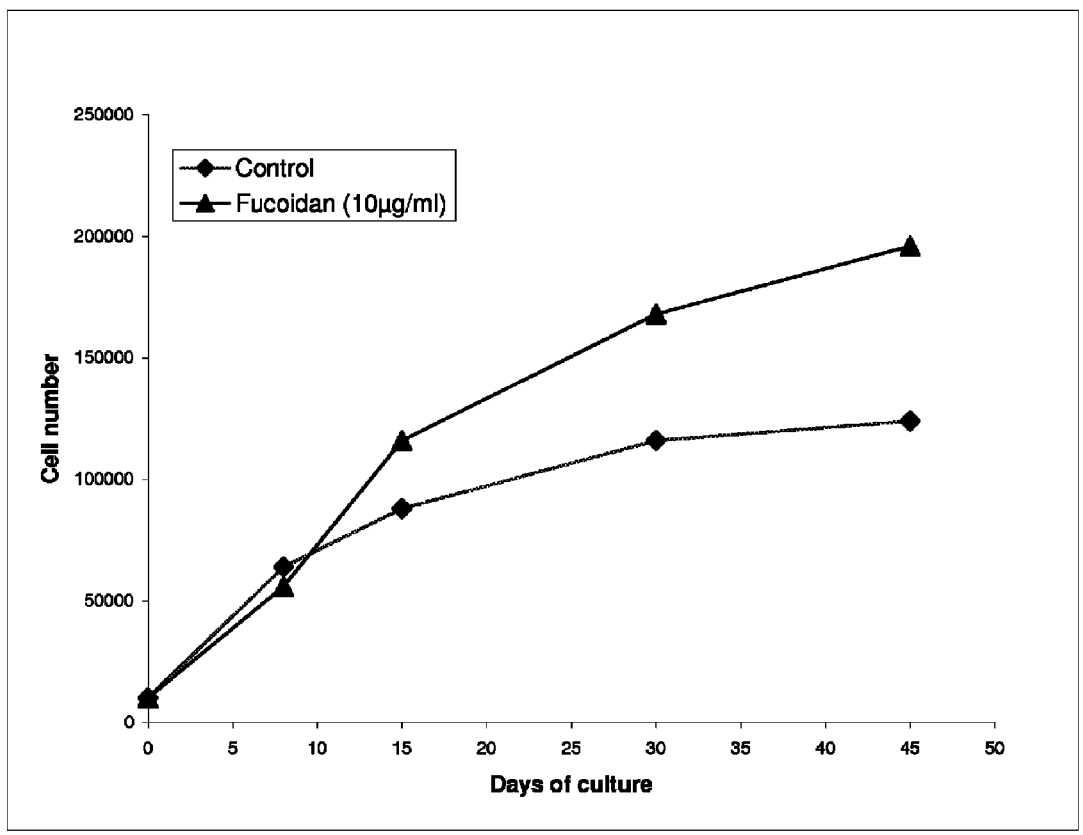

Materials and Methods:
Obtaining the Fucans:

The fucans used in the invention are extracted from Pheophyceae or brown algae (*Ascophyllum nodosum*) according to methods already described (according to Black et al., J. Sci. Food Agric., 3, 122-129, 1952 or according to Nishino et al., Carbohyd. Res., 186, 119-129, 1989) The low-molecular-weight fucans (LMWFs) used are obtained by methods already described: by controlled hydrolysis followed by preparative fractionation on permeable gel or size exclusion (patent EP0403377) or by radical depolymerization (patents EP 0 846 129 and EP 1207891).

Obtaining the Osteoblasts:

The human osteoblastic cells originate from bone fragments recovered in the surgical block during fracture reductions. The bone samples are rinsed in PBS until the cellular elements of the blood are removed. Bone plugs are cut up into cubes of 3 to 4 mm, and then placed in culture dishes. A drop of culture medium (DMEM 40% fetal calf serum (FCS), penicillin (100 IU/ml), streptomycin (100 µg/ml), fungizone (2 µg/ml)) is placed on each explant so as to allow adhesion thereof to the plastic of the dish. The culture dish is then placed in an incubator (37° C., air (95%)/$CO_2$ (5%)) for 1 to 2 hours. The explants are then covered with DMEM culture medium comprising 20% of FCS. This medium is changed every 3 days. The cells migrate out of the explant and colonize the culture dish from the $6^{th}$ day of culture onward, confluence is reached after 4 weeks of culture, and the explants are then removed from the culture dish.

Two-Dimensional Osteoblast Culture

The confluent osteoblasts at the $1^{st}$ culture passage are seeded at a rate of 10 000 cells/ml into 24-well dishes, and then incubated for 24 hours in DMEM medium comprising 10% of FCS supplemented with penicillin and streptomycin. After adhesion and spreading of the cells, the culture media are replaced with DMEM media comprising 10% of FCS, containing or not containing the fucan (10 µg/ml). These culture media are then changed every 3 days. At the $21^{st}$ day of culture, in order to complete the osteoblastic differentiation, β-glycero-phosphate (10 mM) and ascorbic acid 2-phosphate (25 mM) are added. After 8, 15, 30 and 45 days of culture, the culture supernatants are removed in order to study the secretion of matrix metalloproteases. The cells are trypsinized for cell counting or fixed with absolute ethanol (−20° C.), which will subsequently allow morphological and immunocytochemical studies.

Preparation of the Biomaterial for the Cell Culture

The biomaterial is a spongy bone network of bovine origin obtained by cleaning the intertrabecular spaces and eliminating the noncollagen proteins. The biomaterial is pre-cut into small fragments (2 mm ×2 mm), and these fragments are left in absolute ethanol for 48 hours, and then incubated in DMEM for 24 hours at 37° C. (air/5% $CO_2$) in a culture incubator. The bone biomaterials are rehydrated in the culture media in the presence or absence of fucans (50 µg/ml).

Culturing of Osteoblasts in the Bone Biomaterial

Normal human osteoblasts are seeded into 24-well culture dishes (20 000 cells/well) containing the bone biomaterials which may or may not be impregnated with fucans. These grafts are maintained in a "mineralizing" culture medium composed of DMEM, fetal calf serum (10%), ascorbic acid (50 µg/ml), insulin (5 µg/ml) and transferrin (5 µg/ml). Throughout the duration of the experiment, this culture medium is renewed every 3 days. The grafts thus obtained are removed from the culture dishes after 10 or 30 days of culture, fixed, and prepared for the histological studies and studies by scanning electron microscopy.

GIEMSA-Staining of the Cells

This staining makes it possible to visualize the nucleus and the cytoplasm. After fixing, the cells are covered for 2 minutes with prefiltered GIEMSA stain (Merck). The excess stain is removed by successive rinsing with distilled water.

Von Kossa Reaction

This reaction makes it possible to visualize the mineral deposits in the cultures. These deposits appear as black areas. The two-dimensional cultures after fixing are rinsed with distilled water and then incubated for 30 min in a solution of silver nitrate (5%). After rinsing with distilled water, the material is exposed to sunlight.

Visualization of Alkaline Phosphatase Activity in situ

The cells are rinsed with PBS and then incubated in a buffer solution (Tris-HCl (0.05M), pH=9.5, $MgSO_4$ (0.1%), naphthyl phosphate (0.1%), Fast red (0.1%)) for 1 hour at ambient temperature. The supernatant is removed and the wells are rinsed with distilled water 2 to 3 times. The areas with positive alkaline phosphatase activity appear brown.

Immunodetection of Collagen Type I

The cells or the sections of bone biomaterial are rinsed with PBS and then incubated in a solution of $CH_3OH$ (80%)/$H_2O_2$ (20%) for 10 minutes in order to inactivate the endogenous peroxidases. The wells or the sections are rinsed with PBS, and then the nonspecific antigenic sites are blocked (0.1% skimmed milk, 10 min). After rinsing, the material is incubated with a mouse anti-human collagen IgG (sigma, $1/40^{th}$) for 1 hour. After rinsing, the material undergoes further incubation with a peroxidase-labeled goat antibody directed against mouse IgGs ($1/60^{th}$) (calbiochem). After rinsing, the peroxidase activity of the areas containing collagen type I is revealed after reaction with 3,3'-diaminobenzidene tetrahydrochloride (Sigma) (15 min in the dark).

Scanning Electron Microscopy

The bone biomaterials are fixed with 4% paraformaldehyde at times 10 and 30 days. After rinsing with PBS and post-fixing with 2% osmium tetroxide for 45 minutes, the biomaterials are rinsed in three successive baths of sodium cacodylate, and then dehydrated with ethanol solutions increasing up to absolute ethanol. Substitution of the alcohol with liquid $CO_2$ is carried out in an apparatus at the critical point. Gold-metallization of the surface of the sample is carried out by cathode spraying under vacuum in order to obtain a conductive surface layer necessary for optimal observation of the sample by scanning electron microscopy.

Results:

Two-Dimensional Cultures

The cells derived from bone explants are considered to be pre-osteoblastic cells which, in culture, will acquire their purely osteoblastic phenotype. This terminal differentiation takes place after several phases, corresponding to a proliferative phase, a matrix synthesis phase and, finally, a maturation and mineralization phase. The end of the proliferation phase is characterized, after confluence, by the appearance of nodules composed of mature osteoblasts in a three-dimensional extracellular matrix. The synthesis of collagen type I is at a maximum at the time these nodules are formed, and then rapidly decreases. The maturation phase is characterized by an increase in the expression of alkaline phosphatase (AP), which reaches its highest point at the beginning of the mineralization phase. Then, with the terminal differentiation of the osteoblastic cells, the expression of the AP decreases.

Proliferation of Osteoblasts in Two-Dimensional Culture

The addition of fucans to the culture medium greatly stimulates the proliferation of the osteoblastic cells (+45% at 30 days, +60% at 45 days, cf. FIG. 1)).

Alkaline Phosphatase

The kinetics of expression of alkaline phosphatase (AP) by the osteoblasts in culture make it possible to assess the progression of these cells along their differentiation pathways. The appearance of alkaline phosphatase in the cultures marks the beginning of osteoblast differentiation, whereas the mature osteoblasts no longer express this enzyme.

Figure 2:
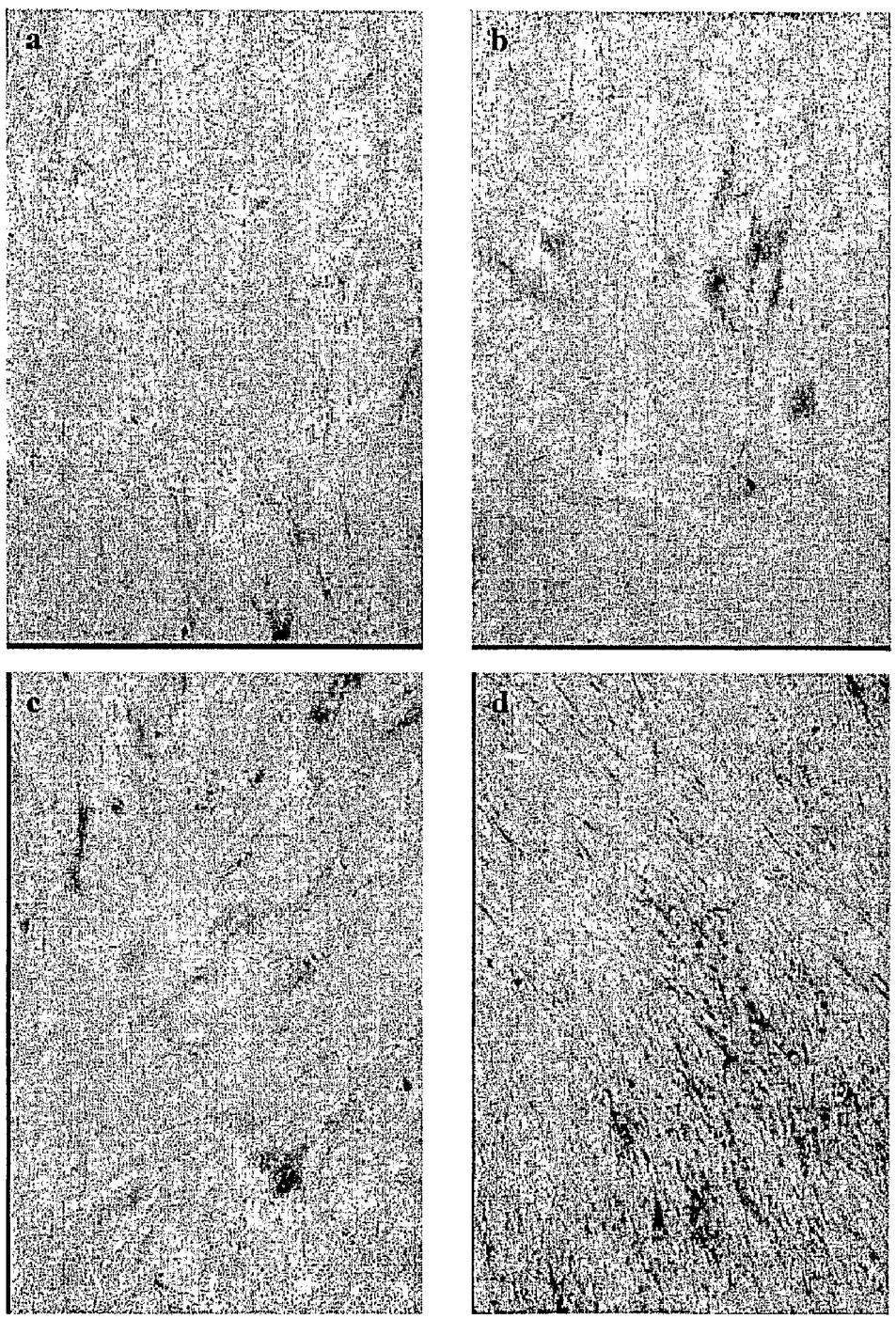
Figure 3:
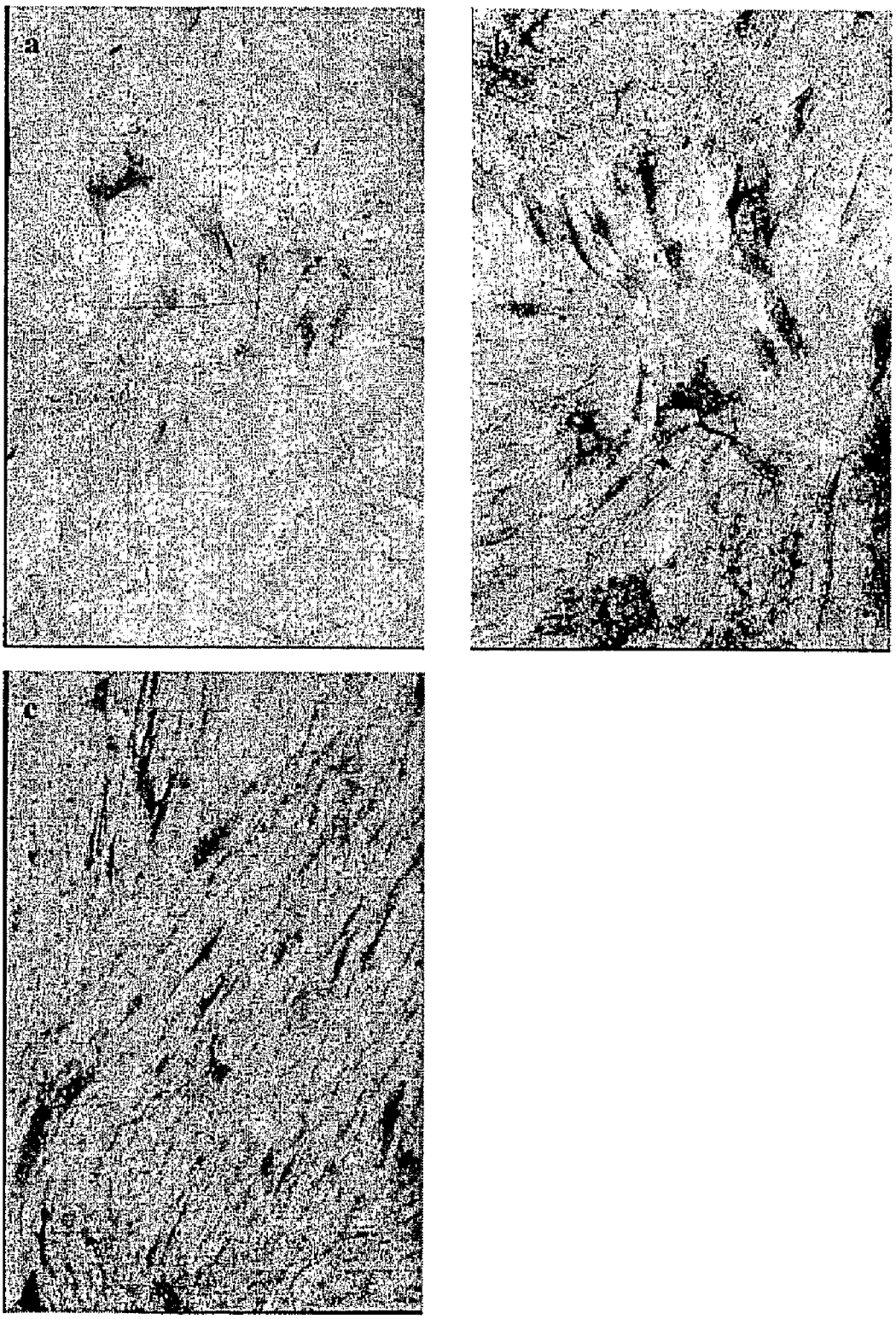

The expression of AP in the control cultures is observed from 15 days of culture onward (FIG. 2a) and is at a maximum at 45 days (FIG. 2d); this expression is much earlier in the cultures incubated in the presence of fucans (10 µg/ml) (cf. FIGS. 3a, 3b, 3c). In fact, in the presence of fucans, the expression of AP is observed from 8 days of culture onward (FIG. 3a), reaches its maximum after 15 days (FIG. 3b), and has clearly decreased in the cultures observed at the $30^{th}$ day (FIG. 3c). Observation of AP expression is no longer possible after 45 days of culture in the presence of the fucans, since mineral deposits cover virtually the entire culture dish.

Von Kossa Reaction and Immunodetection of Collagen Type I

Figure 4:
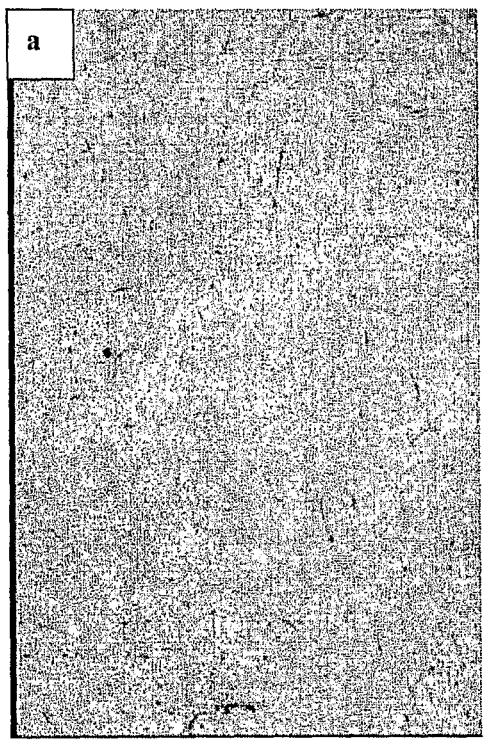
Figure 4:
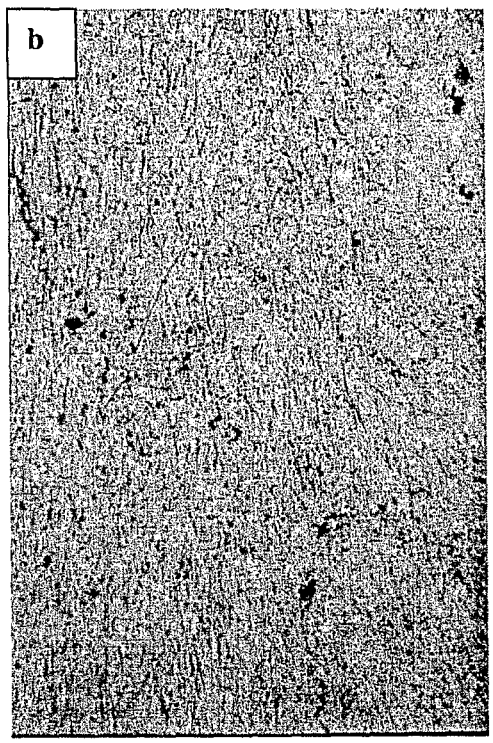
Figure 4:
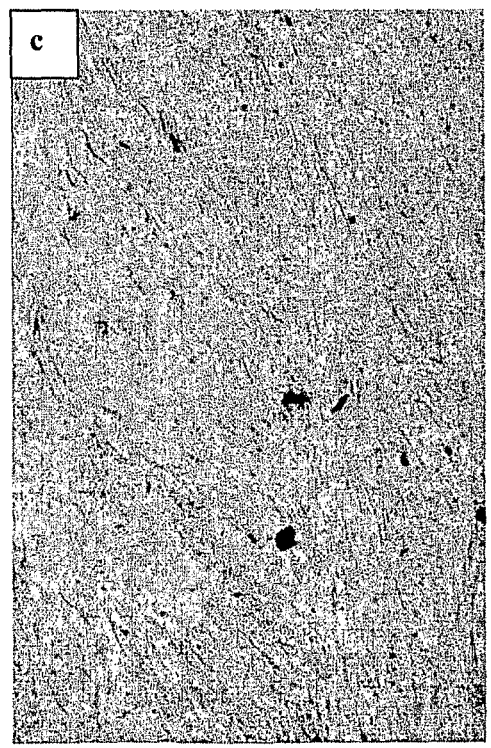
Figure 4:
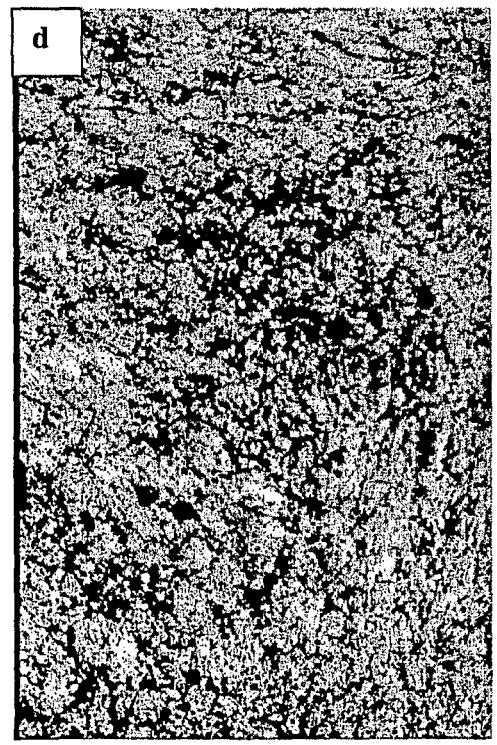

The Von Kossa reaction makes it possible to assess the mineralization state of the extracellular matrix secreted by the osteoblasts in culture (FIG. 4). Some mineralization nodules are detected in the control cultures at 45 days (FIG. 4c), whereas these same nodules are observed from 30 days onward in the cultures in the presence of fucans (FIG. 4b). At 45 days of culture, the extracellular matrix expressed by the osteoblasts incubated with the polysaccharide is virtually entirely mineralized (FIG. 4d).

Figure 5:
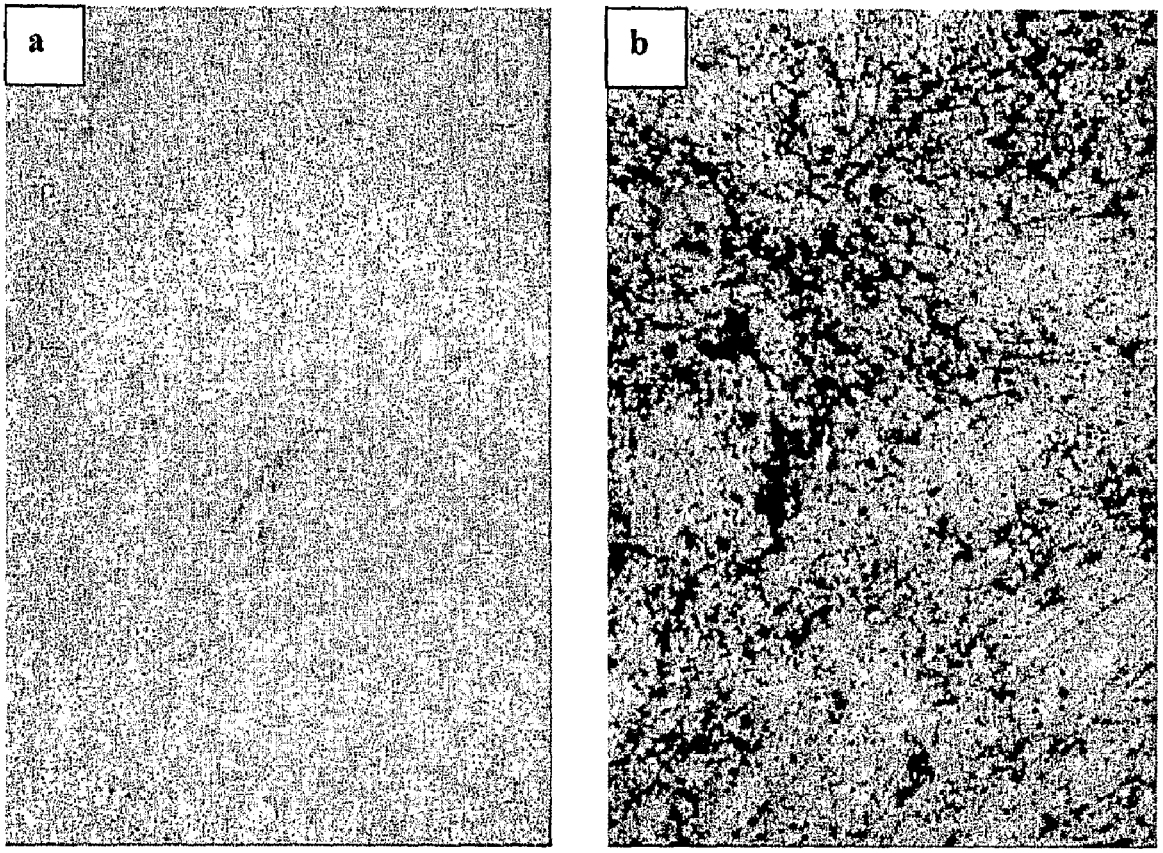
FIGS. 5a, 5b represent photographs of a control culture of osteoblastic cells (FIG. 5a) and of cultures of osteoblastic cells in the presence of 10 μg/ml of fucans (FIG. 5b). After 45 days of culture, immunodetection of collagen type I is carried out on the cells in culture.

After 45 days, the presence of collagen type I is detected in the extracellular matrix of the control cultures or the cultures incubated with the fucan (FIG. 5). The deposit of this fibrillar collagen in the control cultures forms a nonmineralized or barely mineralized network, closely associated with the cell extensions (FIG. 5a). The detection of collagen I in the cultures treated with the fucans shows a collagen network associated with a dense deposit corresponding to the mineral deposit observed after the Von Kossa reaction (FIG. 5b).

Expression of Gelatinase A (MMP-2) and of Collagenase 3 (MMP-13)

The osteoblasts in culture express MMP-2 and MMP-13; MMP-2 is especially expressed at the beginning of culturing, whereas MMP-13 is expressed by the osteoblasts at the end of differentiation. The addition of fucans to the culture appears to decrease the expression of gelatinase A by the osteoblasts, whereas the induced expression of MMP-13 reflects the accelerated differentiation of the cells in the osteoblastic line.

Conclusion:

The addition of fucans to the culture medium accelerates the differentiation of osteoblastic lines.

Three-Dimensional Culture

Scanning Electron Microscopy:

Scanning electron microscopy made it possible to observe the macromolecular structure of the biomaterials and also their colonization by the osteoblasts.

Acellular Biomaterials

Figure 6:
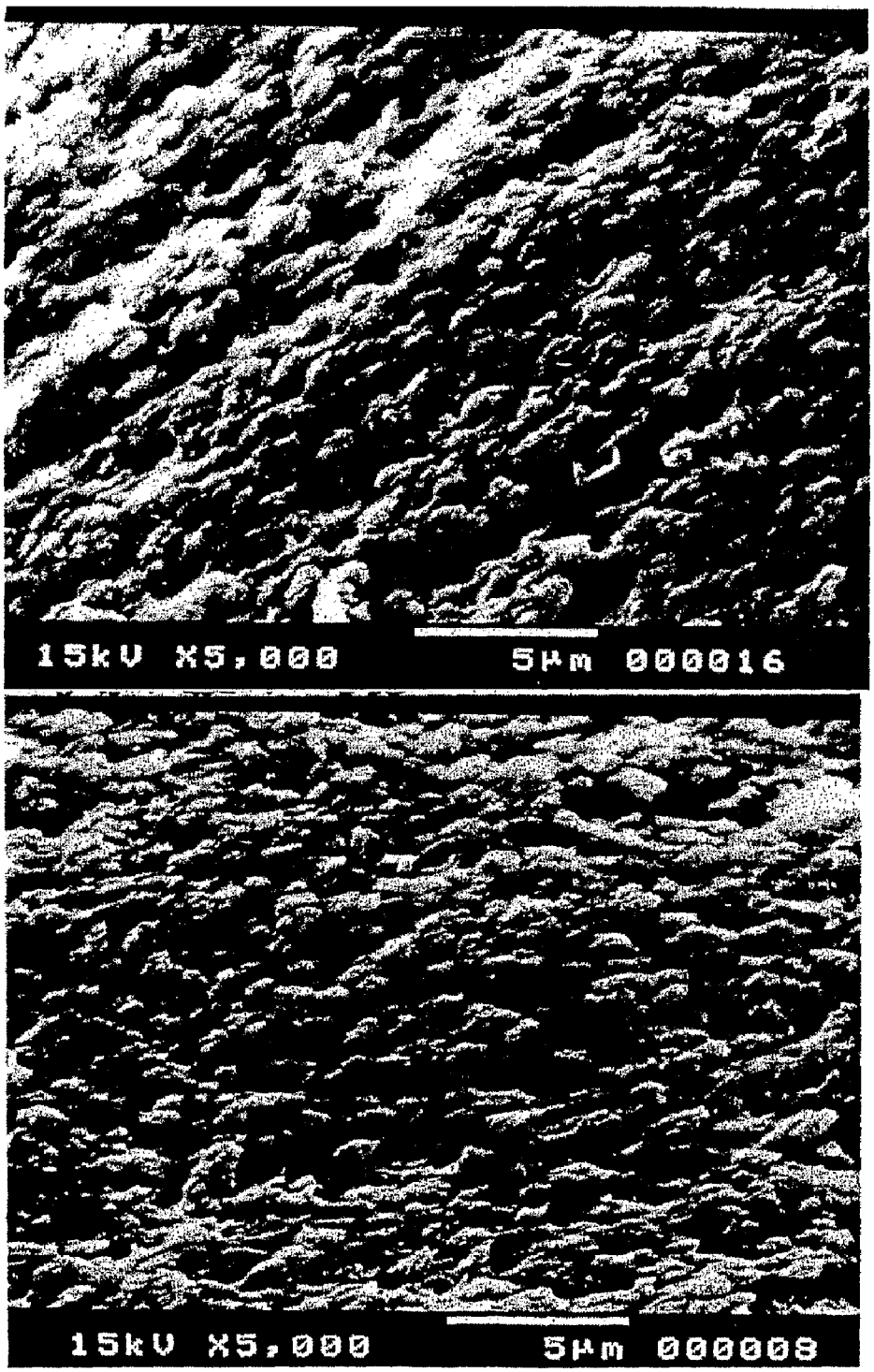
FIGS. 6a and 6b represent images taken by scanning electron microscopy (SEM) of control acellular biomaterials (FIG. 6a) or acellular biomaterials impregnated with fucans (FIG. 6b).

Observation of the biomaterials not seeded with osteoblasts shows that the pretreatment with fucans does not modify the ultrastructure of the bone biomaterial (FIGS. 6a, 6b).

Biomaterials Seeded With Osteoblasts

Figure 7:
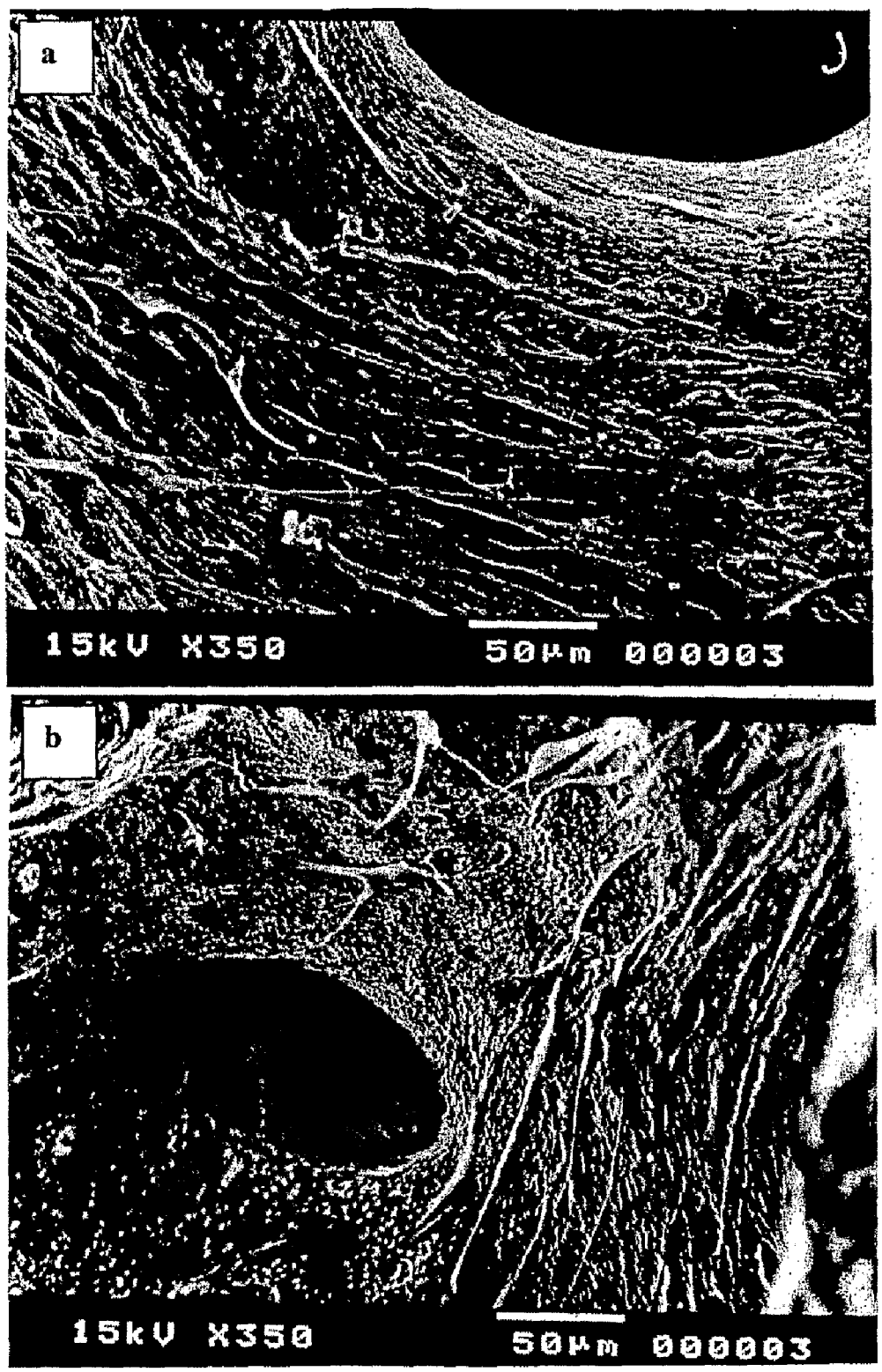
FIGS. 7a and 7b represent images taken by scanning electron microscopy (SEM) of control biomaterials (FIG. 7a) or biomaterials impregnated with fucans (FIG. 7b), on which osteoblasts have been cultured for 10 days.

At 10 days of culture, the cells are adherent to the surface of the biomaterials impregnated or not impregnated with the fucans. These cells have a flattened cell body, which adheres to the collagen network, from where thin and elongated pseudopods are sent out, making it possible to complete the adhesion to the extracellular matrix (FIG. 7).

Figure 8:
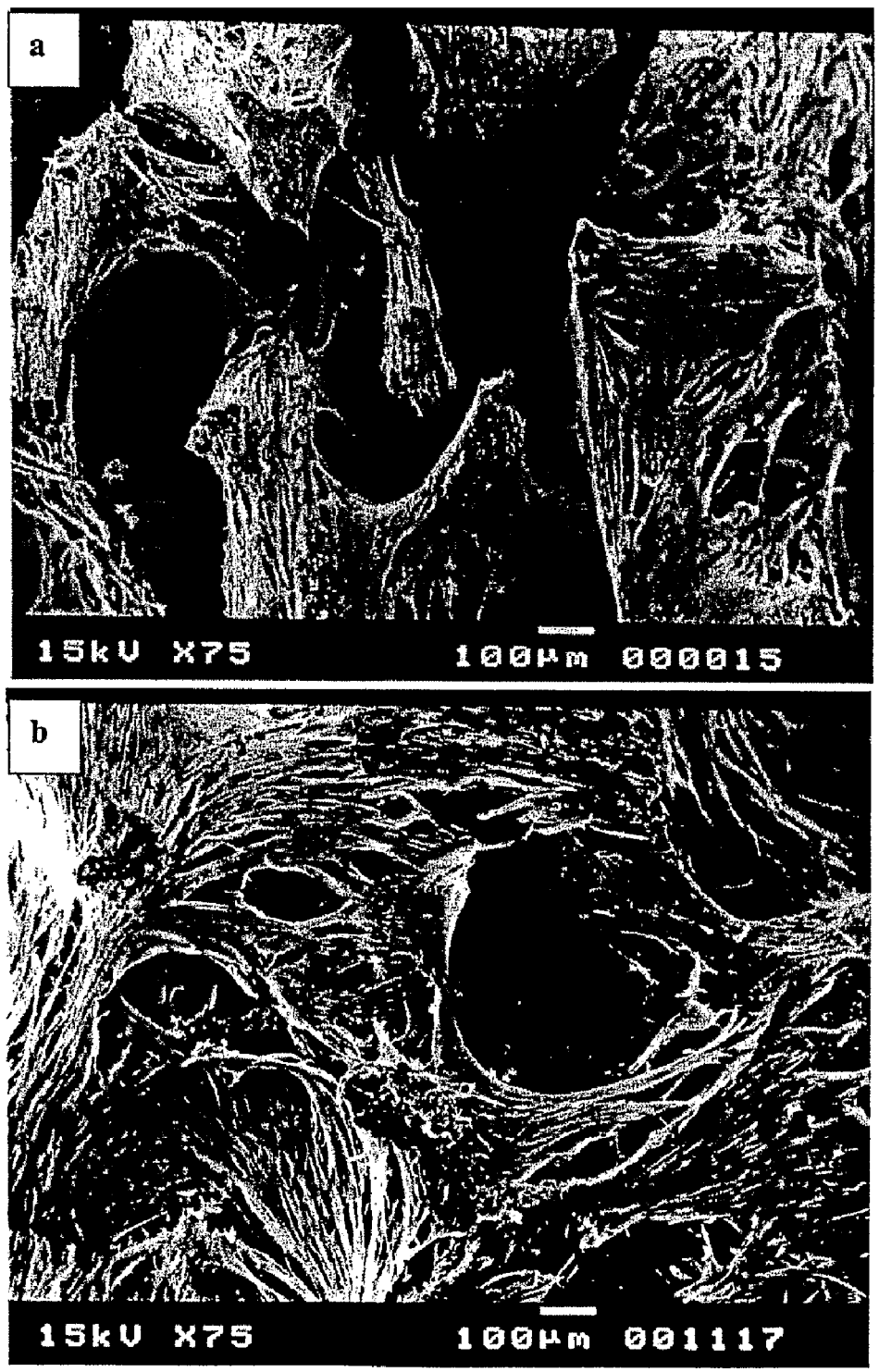
FIGS. 8a and 8b represent images taken by scanning electron microscopy (SEM) of control biomaterials (FIG. 8a) or biomaterials impregnated with fucans (FIG. 8b), on which osteoblasts have been cultured for 30 days.
Figure 9:
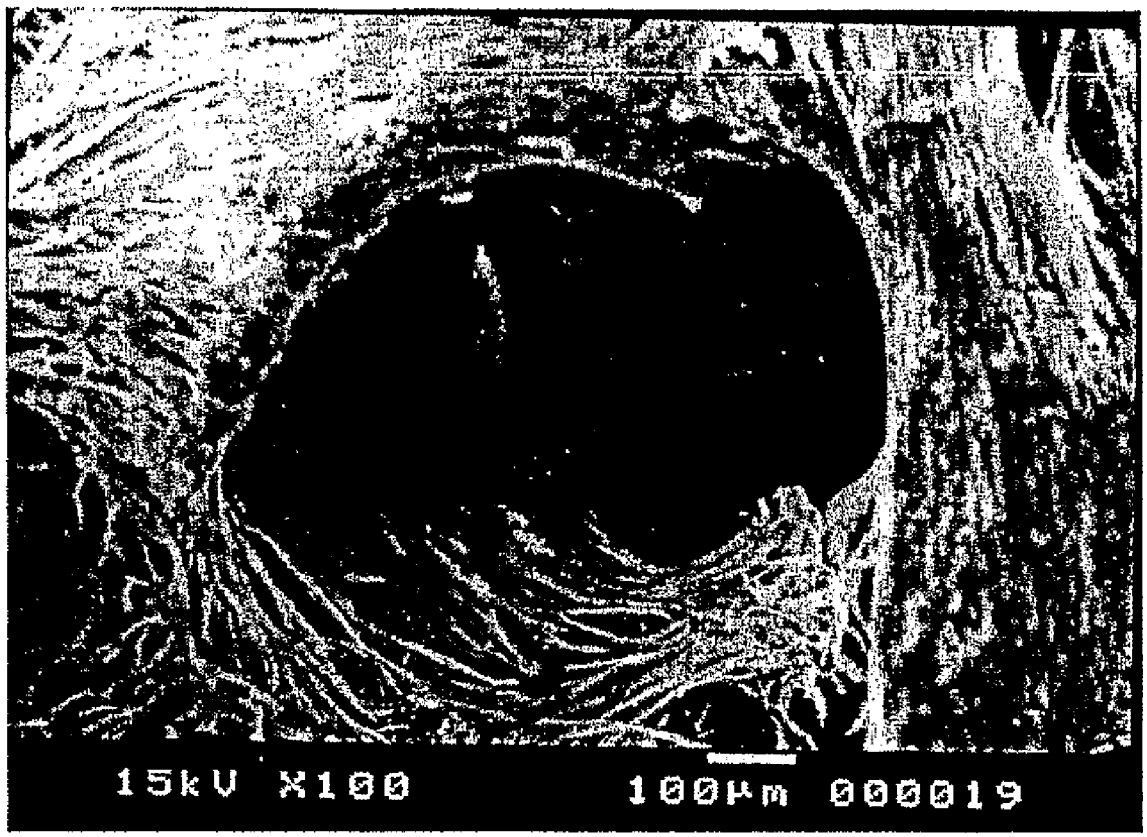
FIG. 9 shows the depth of the biomaterials impregnated with the fucans, on which osteoblasts have been cultured for 30 days.

After 30 days of culture, the cellularity of the control biomaterials and the biomaterials comprising the fucans is much greater than that observed after 10 days, which implies osteoblast proliferation actually within the collagen matrix (FIG. 8). Furthermore, at 30 days of culture, the cell density of the biomaterials comprising the fucans (FIG. 8b) is much higher than that observed for the untreated biomaterials (FIG. 8a). In fact, without fucan, the osteoblasts (FIG. 8a) do not occupy the entire volume of the biomaterial; the pores of the biomaterial remain visible. After impregnation with the fucans, the biomaterials exhibit a high cell density and the pores are to a large extent closed up by the cells (FIG. 8b). The osteoblasts colonize these pores deeply and form bridges on either side of their edges (FIG. 9).

Figure 10:
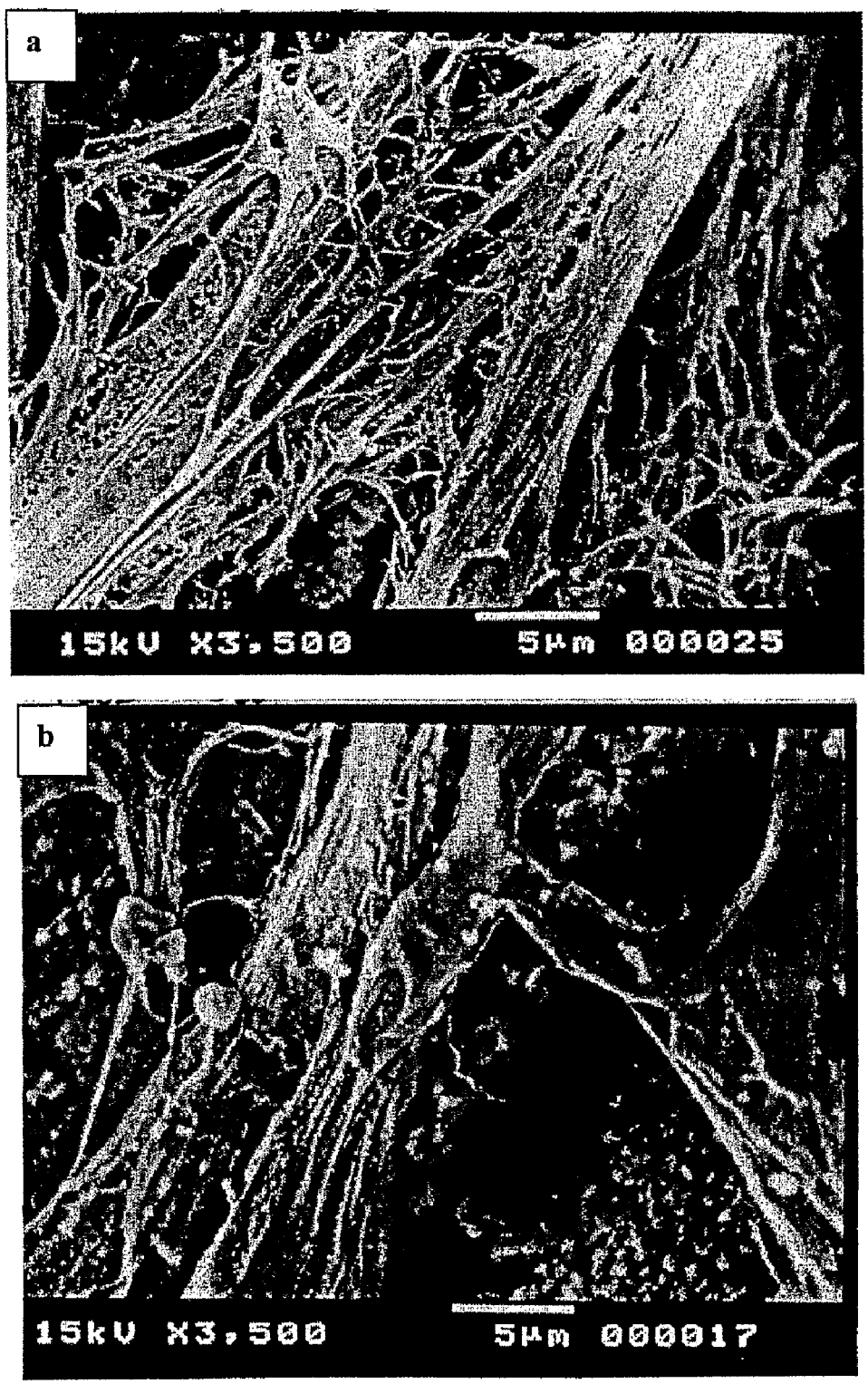
FIGS. 10a and 10b represent images taken by scanning electron microscopy (SEM) of control biomaterials (FIG. 10a) or biomaterials impregnated with fucans (FIG. 10b), on which osteoblasts have been cultured for 10 days, and showing the extracellular matrix secreted by the cells.

The presence of filamentous extracellular material is observed in contact with the cells. This corresponds to the secretion of a fibrillar extracellular matrix by the osteoblasts. Furthermore, the presence of a globular extracellular material in contact with the osteoblasts and the filamentous extracellular matrix is observed (FIG. 10b). This corresponds to the calcified matrix.

Conclusions

The impregnation of the bone biomaterial with the fucans does not modify cell adhesion.

The impregnation of the bone biomaterial with the fucans stimulates osteoblast proliferation.

The impregnation of the bone biomaterial with the fucans accelerates mineralization of the extracellular matrix secreted by the osteoblasts.

The invention claimed is:

1. A bone substitute having an activity on bone regeneration, comprising a biomaterial and fucans, the fucans having an average molecular mass of between 5000 and 100,000 g/mol, wherein said biomaterial comprises one or more materials chosen from the group consisting of titanium, deproteinated and/or demineralized bone, coral, calcium phosphate ceramic, hydroxyapatite, beta-tricalcium phosphate and bioactive glass.

2. The bone substitute as claimed in claim 1, wherein said fucans are obtained from a brown alga.

3. The bone substitute as claimed in claim 1, wherein said bone substitute further comprises one or more growth factors chosen from the group consisting of fibroblast growth factors (FGFs), transforming growth factors (TGFs), insulin growth factors I (IGFs), platelet derived growth factors (PDGFs), bone morphogenic proteins (BMPs) and vascular endothelial growth factors (VEGFs).

4. The bone substitute as claimed in claim 1, wherein said bone substitute further comprises one or more cytokines chosen from the group consisting of interleukin 1, interleukin 4, interleukin 6, tumor necrosis factor-alpha, granulocyte-macrophage colony-stimulating factor and macrophage colony-stimulating factor.

5. The bone substitute as claimed in claim 1, wherein the surface of said biomaterial is covered with a coating comprising said fucans.

6. The bone substitute as claimed in claim 1, wherein said biomaterial is impregnated with said fucans.

7. The bone substitute as claimed in claim 1, wherein said bone substitute further comprises osteocompetent cells derived from bone marrow, from bone or from the periosteum.

8. The bone substitute as claimed in claim 1, wherein said fucans have an average molecular mass of between 10,000 and 40,000 g/mol.

9. A method for preparing a bone substitute as claimed in claim 1, comprising a step of covering the surface of said biomaterial with a coating comprising said fucans or impregnating said biomaterial with said fucans.

10. The method as claimed in claim 9, further comprising colonizing said bone substitute with osteocompetent cells derived from bone marrow, from bone or from the periosteum.

11. The method as claimed in claim 9, wherein said fucans have an average molecular mass of between 10,000 and 40,000 g/mol.

12. A method for bone repair or regeneration in a subject comprising a step of implanting a bone substitute as claimed in claim 1 in a bone defect present in the subject.

13. The method as claimed in claim 12, wherein the bone defect is due to a pathology, to an accident or to a surgical procedure.

14. The method as claimed in claim 12, wherein said fucans have an average molecular mass of between 10,000 and 40,000 g/mol.

* * * * *